US007611509B2

(12) United States Patent
Van Wyk

(10) Patent No.: US 7,611,509 B2
(45) Date of Patent: Nov. 3, 2009

(54) ELECTROSURGICAL DEVICE

(75) Inventor: Robert A. Van Wyk, Largo, FL (US)

(73) Assignee: Electromedical Associates, Bethesda, MD (US)

(*) Notice: Subject to any disclaimer, the term of this patent is extended or adjusted under 35 U.S.C. 154(b) by 221 days.

(21) Appl. No.: 11/133,904

(22) Filed: May 21, 2005

(65) Prior Publication Data
US 2006/0293653 A1 Dec. 28, 2006

(51) Int. Cl.
*A61B 18/18* (2006.01)
(52) U.S. Cl. .............................. 606/41; 606/37; 606/39; 606/40; 606/45
(58) Field of Classification Search ............. 606/41–50, 606/32, 1, 37, 40; 128/898
See application file for complete search history.

(56) References Cited

U.S. PATENT DOCUMENTS

| 4,674,499 | A | | 6/1987 | Pao | |
|---|---|---|---|---|---|
| 4,682,596 | A | | 7/1987 | Bales | |
| 5,195,959 | A | | 3/1993 | Smith | |
| 5,261,905 | A | * | 11/1993 | Doresey, III | 606/45 |
| 5,277,696 | A | | 1/1994 | Hagen | |
| 5,782,829 | A | * | 7/1998 | Swiantek et al. | 606/46 |
| 6,056,747 | A | * | 5/2000 | Saadat et al. | 606/50 |
| 6,066,134 | A | | 5/2000 | Eggers | |
| 6,419,684 | B1 | * | 7/2002 | Heisler et al. | 606/170 |
| 6,565,560 | B1 | * | 5/2003 | Goble et al. | 606/41 |
| 6,575,968 | B1 | | 6/2003 | Eggers | |
| 6,796,982 | B2 | * | 9/2004 | Carmel et al. | 606/41 |
| 6,840,937 | B2 | | 1/2005 | Van Wyk | |
| 6,899,712 | B2 | * | 5/2005 | Moutafis et al. | 606/49 |
| 6,921,398 | B2 | | 7/2005 | Carmel et al. | |
| 6,921,399 | B2 | * | 7/2005 | Carmel et al. | 606/41 |
| 6,955,676 | B2 | * | 10/2005 | Quick | 606/45 |
| 7,066,936 | B2 | * | 6/2006 | Ryan | 606/45 |
| 7,150,748 | B2 | * | 12/2006 | Ebbutt et al. | 606/50 |
| 7,166,103 | B2 | | 1/2007 | Carmel et al. | |
| 2002/0038122 | A1 | * | 3/2002 | Peters | 606/45 |
| 2003/0088243 | A1 | * | 5/2003 | Carmel et al. | 606/41 |
| 2004/0049183 | A1 | * | 3/2004 | Ellman et al. | 606/45 |
| 2004/0106919 | A1 | * | 6/2004 | Hood | 606/41 |
| 2004/0193150 | A1 | | 9/2004 | Sharkey et al. | |
| 2005/0065510 | A1 | | 3/2005 | Carmel et al. | |
| 2005/0234446 | A1 | | 10/2005 | Van Wyk et al. | |
| 2006/0122680 | A1 | | 6/2006 | Auth et al. | 607/122 |
| 2006/0184165 | A1 | * | 8/2006 | Webster et al. | 606/41 |
| 2006/0235377 | A1 | * | 10/2006 | Earley et al. | 606/41 |
| 2006/0259031 | A1 | | 11/2006 | Carmel et al. | |
| 2009/0069802 | A1 | * | 3/2009 | Garito et al. | 606/37 |

* cited by examiner

*Primary Examiner*—Michael Peffley
*Assistant Examiner*—Victoria W Chen
(74) *Attorney, Agent, or Firm*—Chalin Smith; Smith Patent Consulting, LLC

(57) ABSTRACT

An electrosurgical electrode capable of vaporization, coagulation, desiccation or cutting of tissue is disclosed. The probe has a first portion configured for tissue vaporization, and a second portion configured for tissue desiccation or coagulation. Simultaneous vaporization and desiccation may be achieved, the balance between the effects being controlled by the orientation and motions of the electrode. The electrode may have irrigation and aspiration means.

38 Claims, 11 Drawing Sheets

ELECTROSURGICAL DEVICE

BACKGROUND OF THE INVENTION

The present invention relates generally to the field of electrosurgery, and, more particularly, to high efficiency surgical devices and methods which use of high frequency (RF) electrical power for cutting, bulk removal by vaporization with externally supplied conductive liquid irrigants.

The present invention provides a system and method for performing electrosurgical cutting, ablation (volumetric tissue vaporization), coagulation or modification within or on the surface of a patient. The system and method of the invention herein disclosed may be used in relatively dry environments, for instance, for oral, otolaryngological, laparoscopic, and dermatologic procedures.

Electrosurgical procedures require a proper electrosurgical generator, which supplies the Radio Frequency (RF) electrical power, and a proper surgical electrode (also known as an electrosurgical probe). Under appropriate conditions the desired surgical effects are accomplished.

Note: in common terminology and as used herein the term "electrode" may refer to one or more components of an electrosurgical device (such as an active electrode or a return electrode) or to the entire device, as in an "ablator electrode". Electrosurgical devices may also be referred to as "probes".

An electrosurgical probe, in general, is composed of a metallic conductor surrounded by a dielectric insulator (for example plastic, ceramic or glass) except for the exposed metallic electrode. The probe electrode is often immersed in a conducting fluid, either filling a natural or created cavity or applied as irrigant to a "dry" site, and is brought in contact with or close proximity to the tissue structure during the electrosurgical procedure. The probe is energized, typically at a voltage of few hundred to a few thousand volts, using an RF generator operating at a frequency between 100 kHz to over 4 MHz. This voltage induces a current in the conductive liquid and nearby tissue. This current heats the liquid and tissue, the most intense heating occurring in the region very close to the electrode where the current density is highest. At points where the current density is sufficiently high, the liquid boils locally and many steam bubbles are created, the steam bubbles eventually insulating part or all of the electrode. Electrical breakdown in the form of an arc (spark) occurs in the bubbles which insulate the electrode. The sparks in these bubbles are channels of high temperature ionized gas, or plasma (temperature of about a few thousand degrees Kelvin). These high current density sparks, heat, vaporize (ablate) or cut the tissue (depending on the specific surgical procedure and the probe geometry) that is in contact with the spark or the adjacent heated fluid.

Many surgical procedures are not performed inside a natural or formed body cavity and as such are not performed on structures submerged under a conductive liquid. In laparoscopic procedures, for instance, the abdominal cavity is pressurized with carbon dioxide to provide working space for the instruments and to improve the surgeon's visibility of the surgical site. Other procedures, such as oral surgery, the ablation and necrosis of diseased tissue, or the ablation of epidermal tissue, are also typically performed in an environment in which the target tissue is not submerged. In such cases it is necessary to provide a conductive irrigant to the region surrounding the active electrode(s), and frequently also to aspirate debris and liquid from the site. Such irrigant may be applied by a means external to the instrument; however, having an irrigation means internal or attached to the instrument generally provides better control and placement. This is also true for aspiration of fluid and debris. External means may be used for aspiration from the site; however, aspiration through the instrument distal end provides improved fluid control and may, in some cases, draw tissue toward the active electrode thereby enhancing performance.

Electrosurgical devices having a means for irrigating a site, and/or means for aspirating fluid, bubbles and debris from a site are well known. Smith in U.S. Pat. No. 5,195,959 teaches an electrosurgical device with suction and irrigation. Bales, et al in U.S. Pat. No. 4,682,596 teach a catheter for electrosurgical removal of plaque buildup in blood vessels, the catheter having lumens for supplying irrigant to the region of the instrument distal tip and for aspirating debris from the region. Hagen in U.S. Pat. No. 5,277,696 teaches a high frequency coagulation instrument with means for irrigation and aspiration from the region of the instrument tip. Pao in U.S. Pat. No. 4,674,499 teaches a coaxial bipolar probe with suction and/or irrigation. Eggers in U.S. Pat. No. 6,066,134 teaches a method for electrosurgical cutting and coagulation which uses a bipolar probe having means for irrigating and aspirating from the region of the probe distal tip. The Eggers device uses the irrigant flow to provide a return path to a return electrode recessed axially a distance away from the active electrode(s).

One application of electrosurgical technique is the removal of a portion of tissue from a vascular surrounding tissue bed in a "dry" environment, that is, in an environment in which conductive irrigant is supplied to the surgical site. Such removal requires the effective vaporization of connecting tissue to allow removal of the tissue portion, and also coagulation of the adjacent remaining tissue to prevent bleeding. Debris and irrigant are removed from the site by aspiration, either by a means external to the electrosurgical instrument or through external means.

It is accordingly an object of this invention to produce an electrosurgical probe which is able to effect the removal of a tissue portion from a surrounding vascular bed while minimizing bleeding.

It is also an object of this invention to produce an electrosurgical probe which has a simple structure so that it is producible at low cost.

It is additionally an object of this invention to produce an electrosurgical probe in which tissue may be either vaporized or coagulated through selection of the probe surface in contact with the tissue.

SUMMARY OF THE INVENTION

These and other objects are achieved in the invention herein disclosed which is an electrosurgical device for the cutting, bulk vaporization, and coagulation of tissue at a surgical site, conductive irrigant being supplied to the site via means within the device, and debris and fluid aspirated from the site by means within the device. The device has a distal tip having a first portion with ribs, grooves, protrusions or other features for creating regions of high current density capable of high efficiency vaporization of tissue, and a second portion having a surface suited for coagulation or thermal treatment of tissue. In use the surgeon affects tissue with the first surface to separate tissue from a surrounding bed, and to vaporize selected tissue. The surgeon affects tissue with the second surface to coagulate the remaining tissue to prevent bleeding. The surgeon may use both surfaces simultaneously. In other embodiments irrigant is supplied by means external to the probe. In still other embodiments aspiration is supplied by means external to the probe.

DESCRIPTION OF THE PREFERRED EMBODIMENTS

Figure 1:
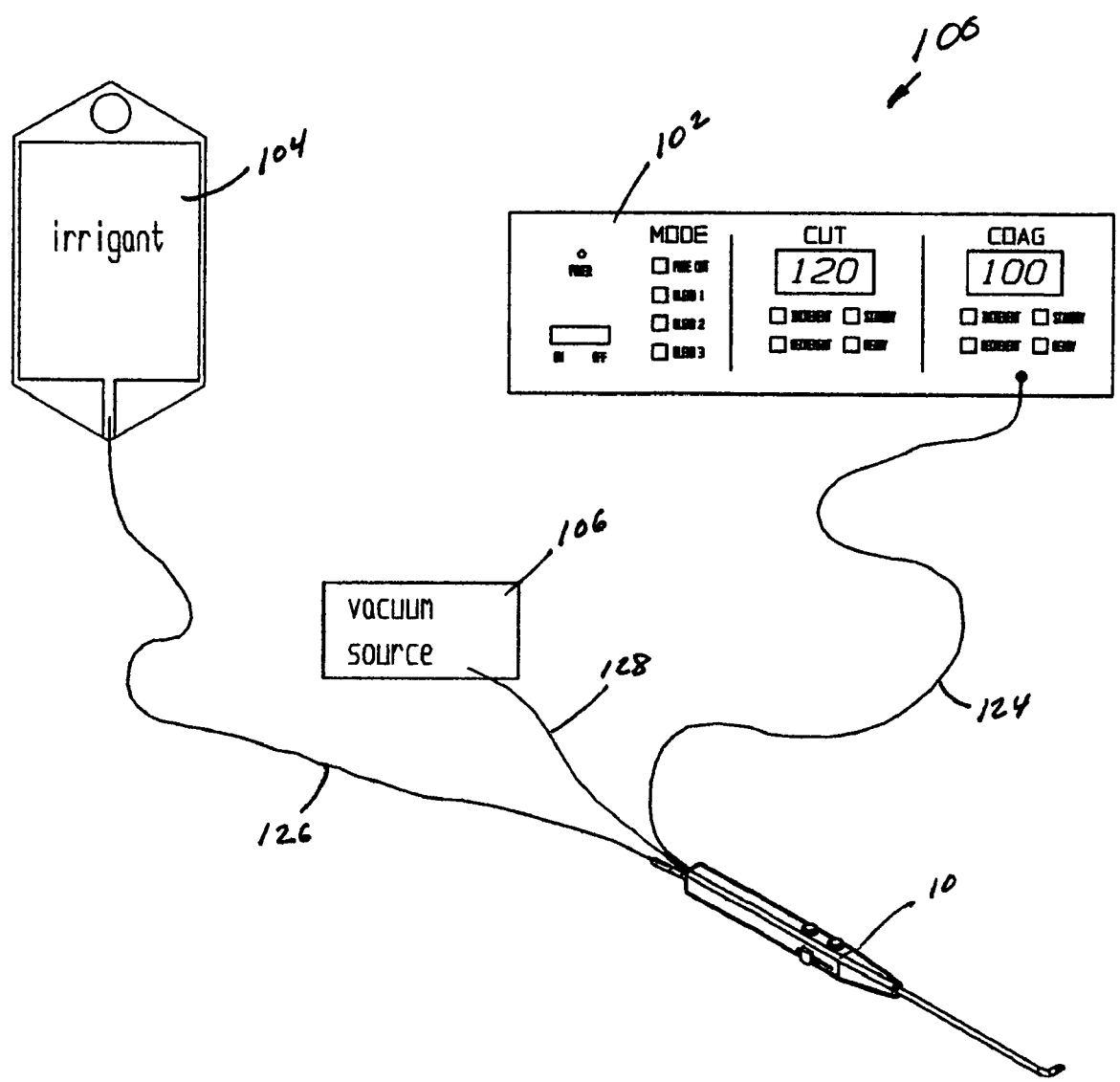
FIG. 1 shows an electrosurgical system formed in accordance with the principles of this invention.

Referring now to the figures, as seen in FIG. 1, electrosurgical system 100 has an electrosurgical generator 102 connected to electrosurgical probe 10 by cable 124, an irrigant source 104 connected by tube 126 to probe 10, and a vacuum source 106 connected by tube 128 to probe 10. Control of the generator by probe 10, and control of the vacuum source and irrigant flow are conventional and not elements of the invention herein disclosed. A return electrode, not shown, is attached to the patient at a site remote from the surgical site.

Figure 2:
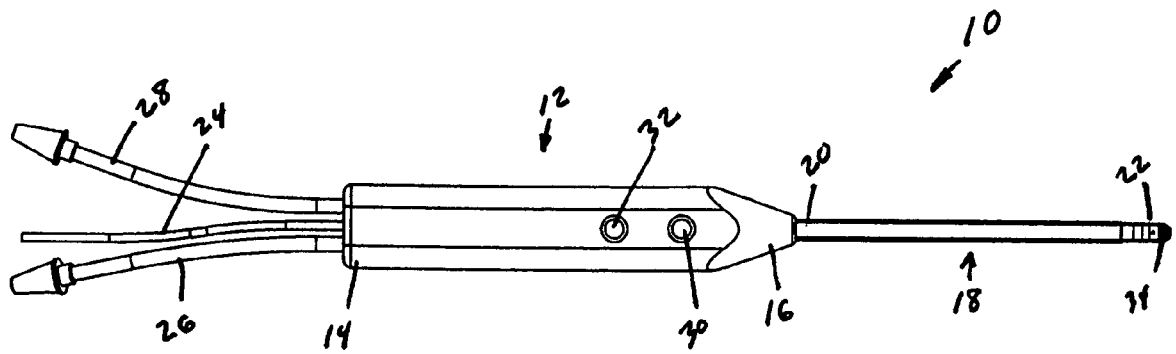
FIG. 2 is a plan view of an electrosurgical probe formed in accordance with the principles of this invention.
Figure 3:
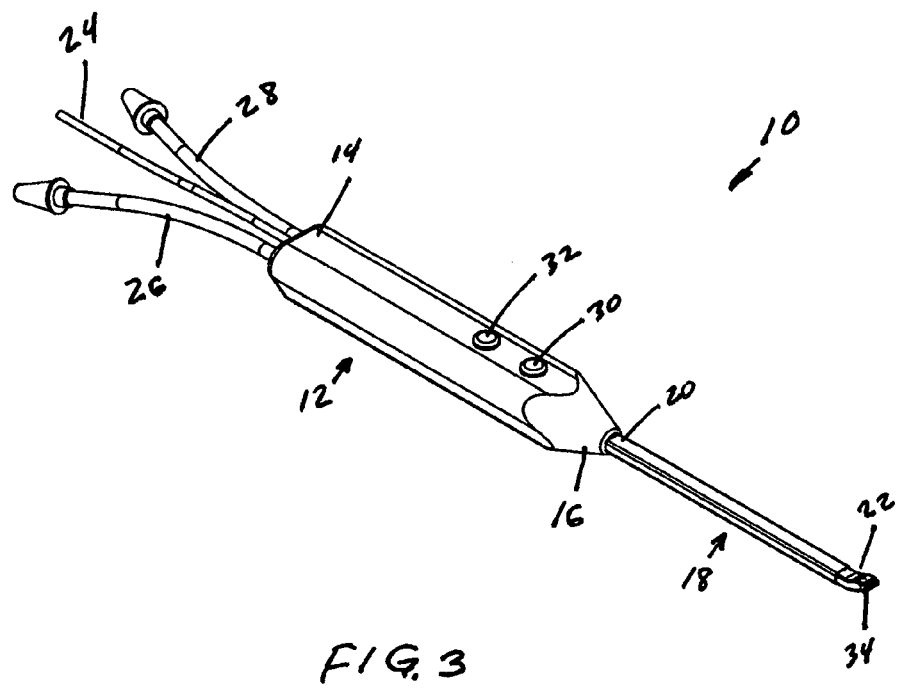
FIG. 3 is a perspective view of the objects of FIG. 2.
Figure 5:
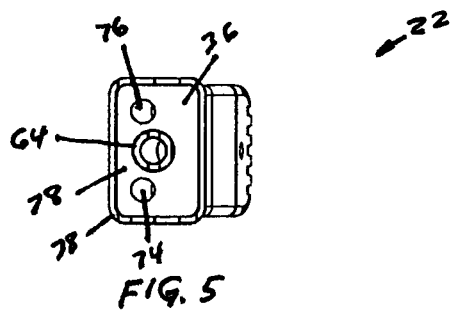
FIG. 5 is a top axial view of the objects of FIG. 4.
Figure 8:
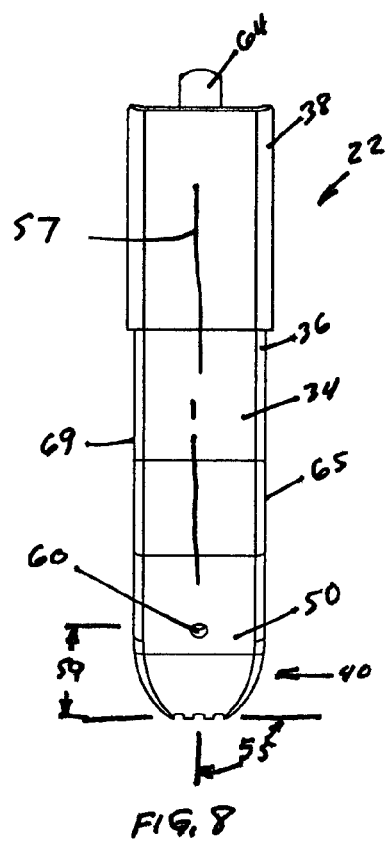
FIG. 8 is an elevational view of the second surface of the objects of FIG. 4 configured for the coagulation or thermal treatment of tissue.
Figure 4:
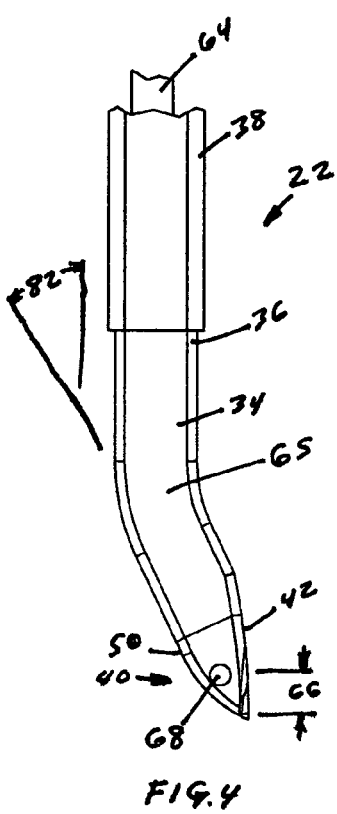
FIG. 4 is an expanded side elevation view of the distal portion of the probe of FIG. 2, the probe being positioned vertically as for use, for instance, in removing a tonsil from the tonsilar bed.
Figure 7:
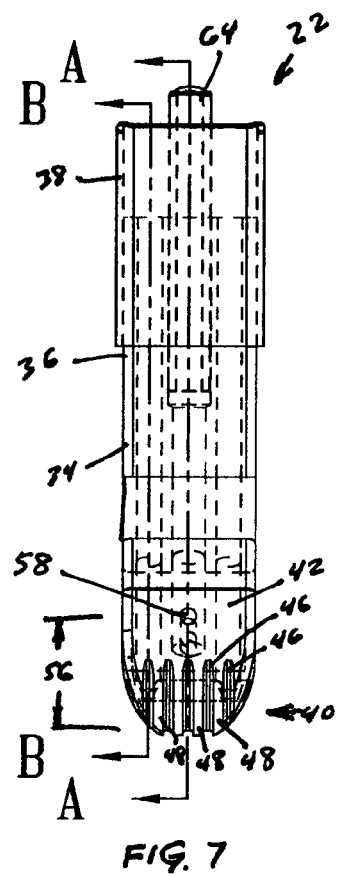
FIG. 7 is an elevational view of the first surface of the objects of FIG. 4 configured for the vaporization of tissue.
Figure 6:
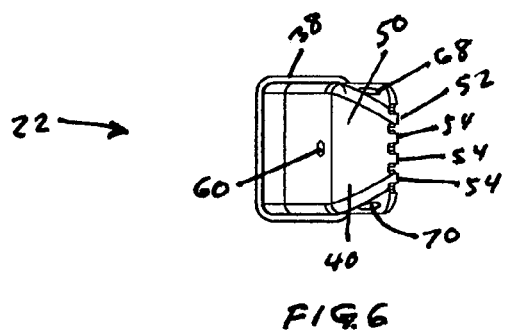
FIG. 6 is a bottom end axial view of the objects of FIG. 4.
Figure 9:
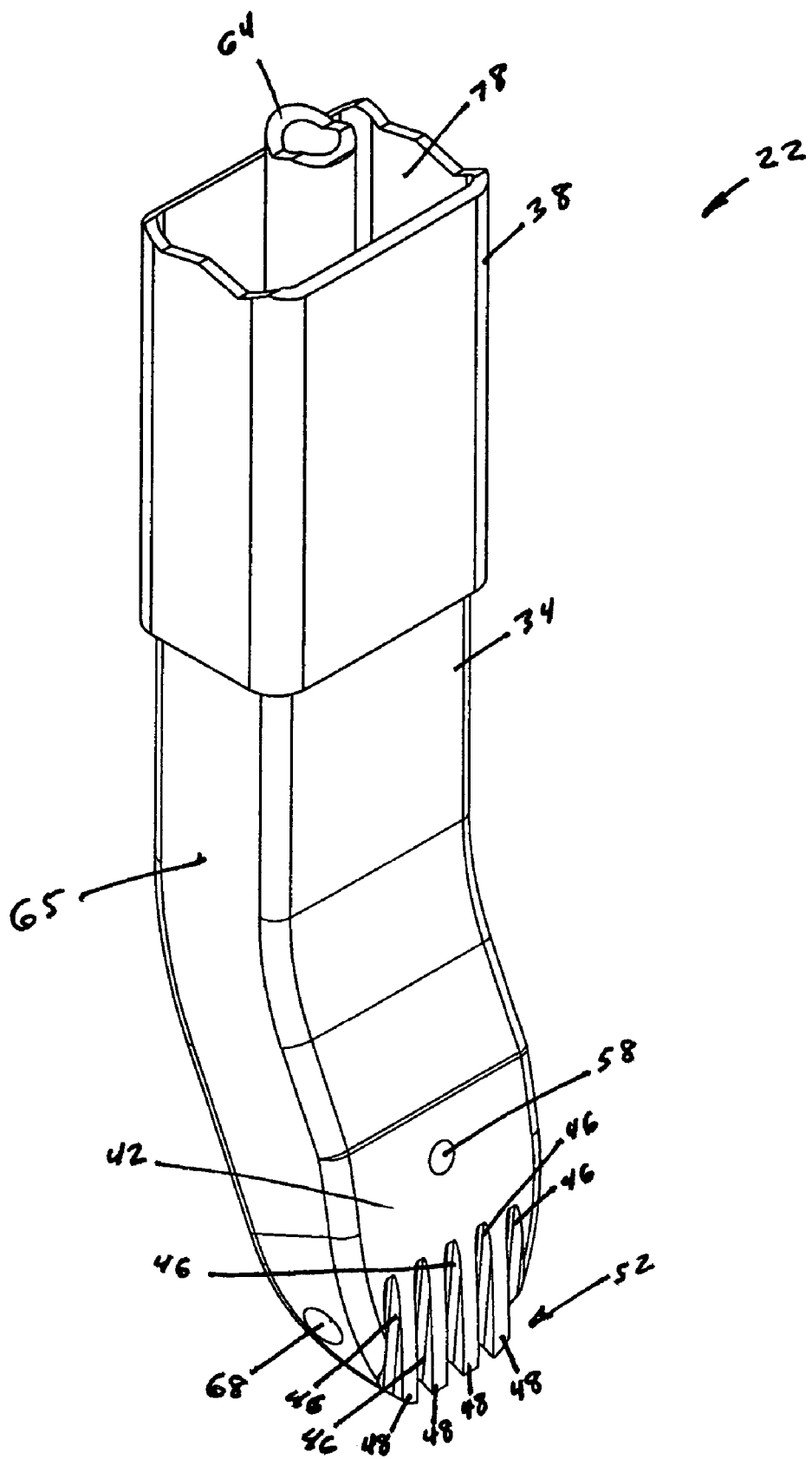
FIG. 9 is a perspective view of the objects of FIG. 4 showing the first surface.
Figure 10:
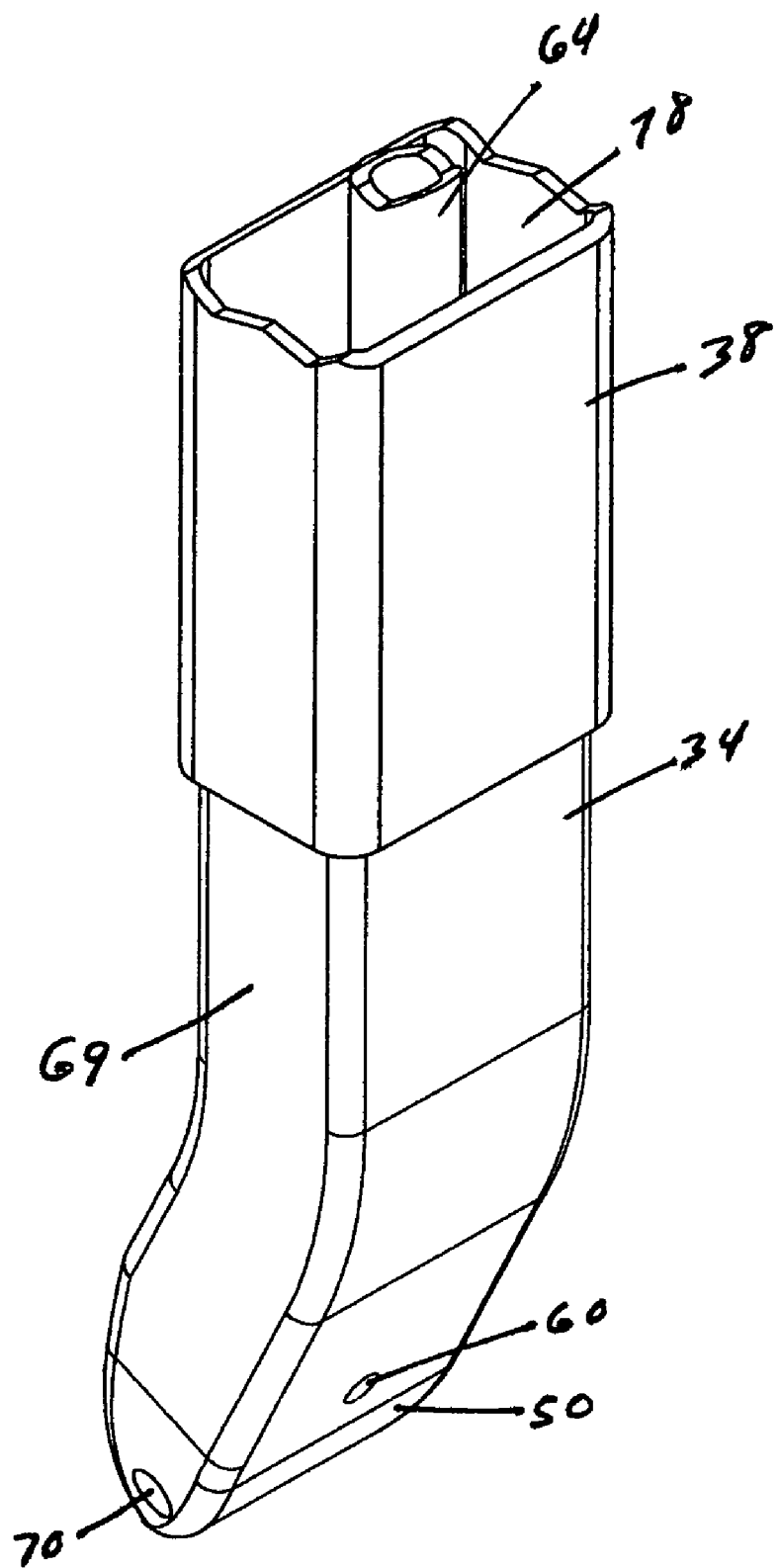
FIG. 10 is a perspective view of the objects of FIG. 4 showing the second surface.

As seen in FIGS. 2 and 3, electrosurgical instrument 10 formed in accordance with the principles of this invention, has a proximal portion 12 forming a handle having a proximal end 14 and a distal end 16, and an elongated distal portion 18 having a proximal end 20 and a distal end 22. Proximal end 20 of distal portion 18 is rigidly affixed to distal end 16 of handle 20. Proximal end 14 of handle 12 has passing therefrom cable 24 which connects to electrosurgical generator 102 (FIG. 1), first tube 26 connects to irrigant source 104, and second tube 28 connects to vacuum source 106. Near distal end 16 of portion 12, first activation button 30 and second activation button 32 are connected via cable 24 to electrosurgical unit 102. Distal end 22 of elongated distal portion 18 comprises an active electrode 34.

Figure 11:
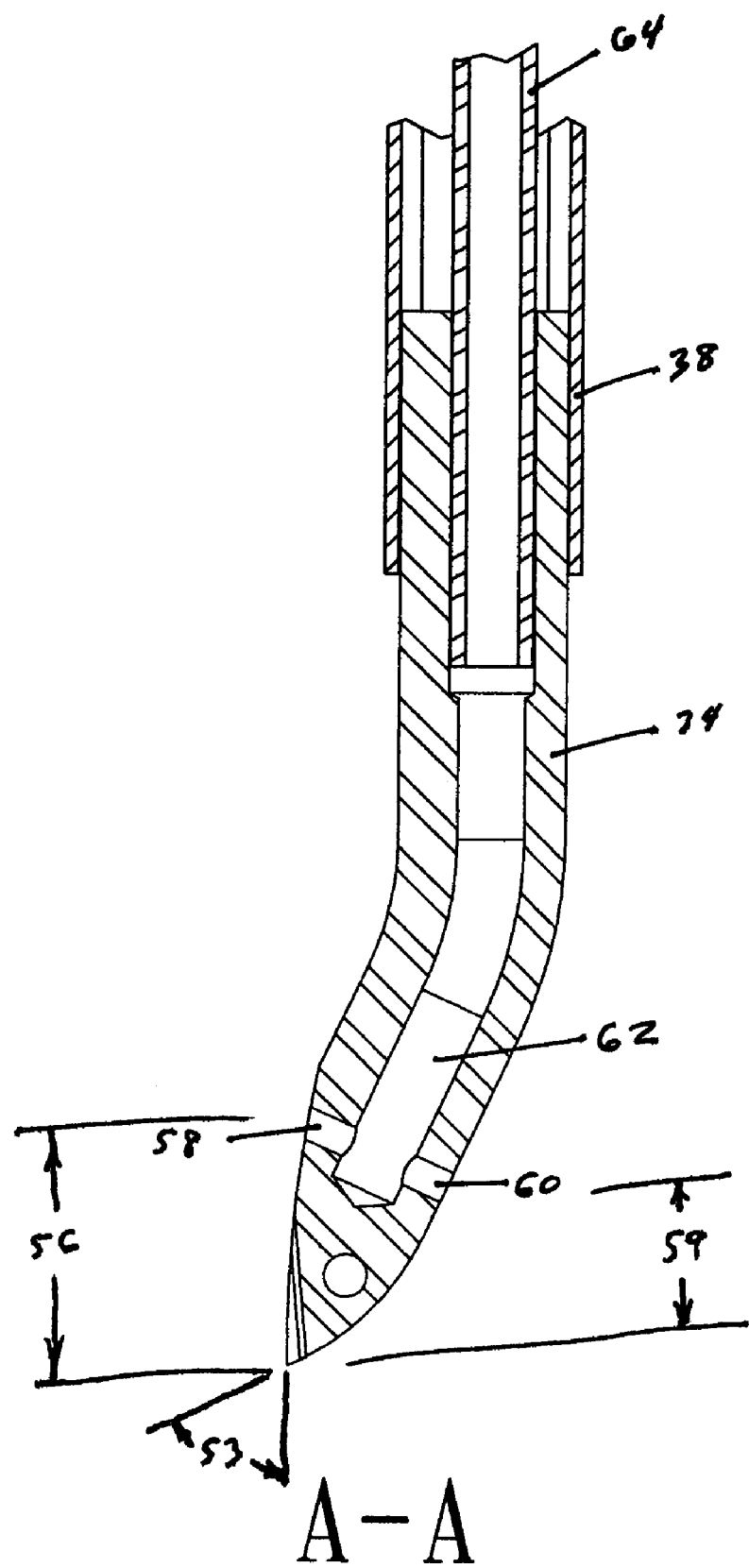
FIG. 11 is an elevational sectional view at location A-A of FIG. 7, in direction A-A showing the irrigation means.
Figure 12:
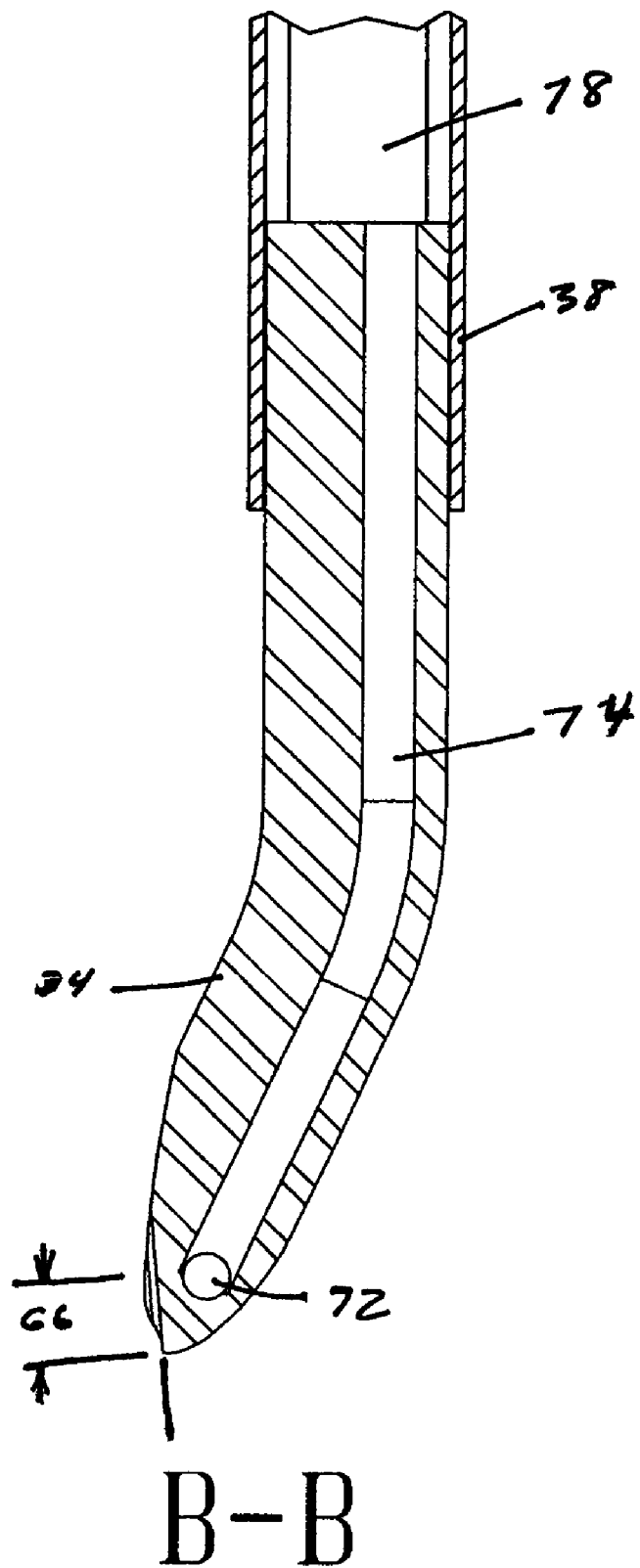
FIG. 12 is an elevational sectional view at location B-B of FIG. 7 in direction B-B showing the aspiration means.
Figure 13:
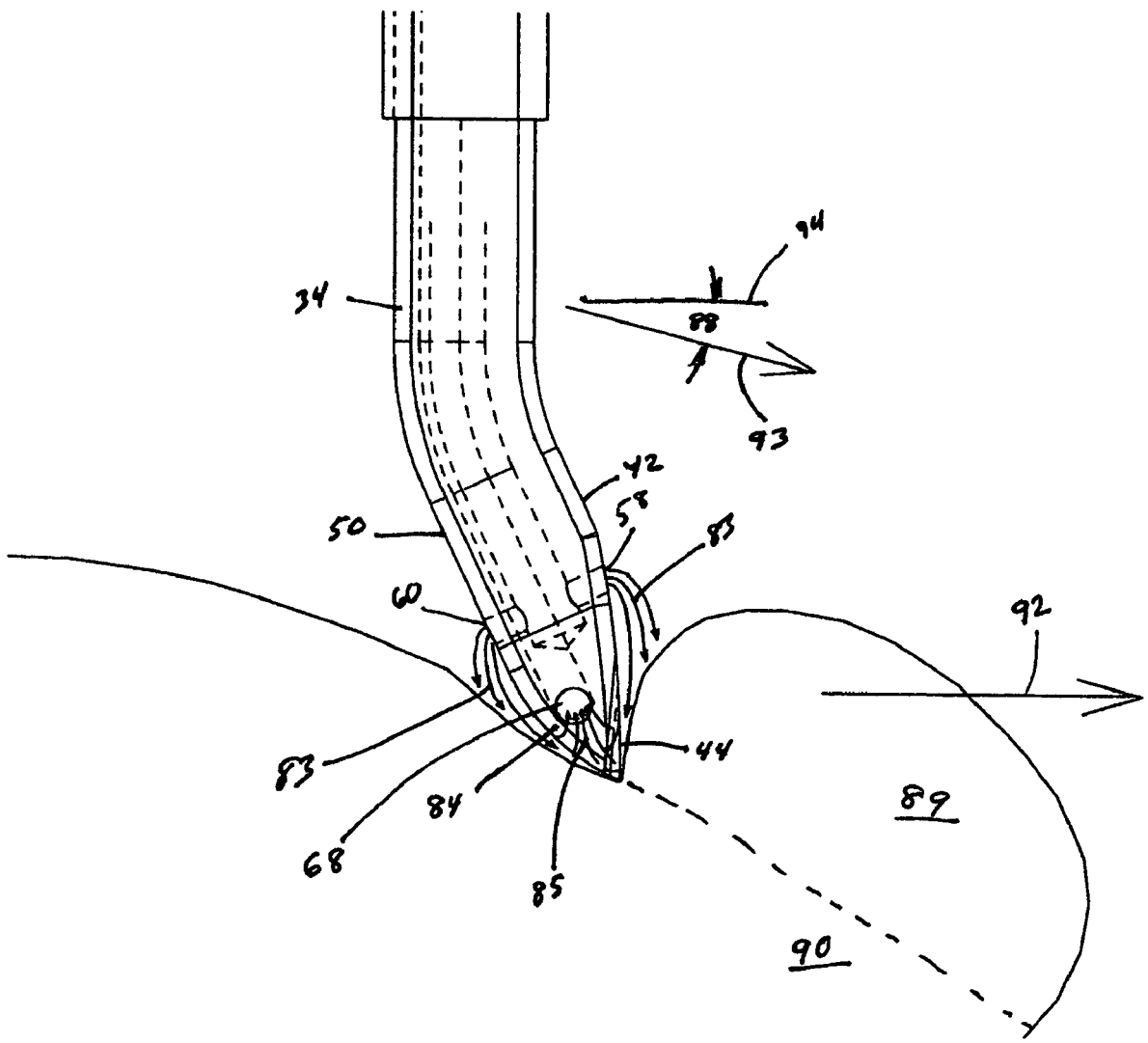
FIG. 13 is an expanded elevational view of the distal portion of the instrument of FIG. 2 during use when primarily vaporizing tissue.

Referring now to FIGS. 4 through 10, distal end 22 of probe 10 has an electrode 34 having a proximal end 36 assembled to rectangular tube 38 which extends from electrode 34 to the handle portion 12 of probe 10, and a distal end 40. Electrode 34 has a first surface portion 42 having a distal portion 44 in which are formed grooves 46 and ribs 48. Electrode 34 has a second surface portion 50 having a smooth convex contour. Distal-most edge 52 formed by the intersection of surfaces 42 and 50 has an included angle 53 and has teeth 54 formed by ribs 48. In a preferred embodiment included angle is between 20 and 110 degrees, and more preferably between 30 and 90 degrees. Edge 52 forms an angle 55 with axis 57 of tube 38 when viewed as in FIG. 8. In a preferred embodiment angle 55 is between 30 and 90 degrees, and more preferably between 45 and 90 degrees. In other embodiments distal-most edge 52 is curvilinear. First surface 42 has formed therein, distance 56 from distal end 40, irrigation port 58. Second surface portion 50 has formed therein, distance 59 from distal end 40, irrigation port 60. Referring now to FIG. 11, irrigation ports 58 and 60 are in communication via lumen 62 with tube 64 which is connected via means within probe handle 12 to tube 26 and there through to irrigant source 104. First lateral surface 65 has positioned therein distance 66 from distal end 40 aspiration port 68. Second lateral surface 69 has positioned therein distance 66 from distal end 40 aspiration port 70. Distance 66 is preferably between one and four millimeters, and more preferably between one and two millimeters. Referring now to FIG. 12, aspiration ports 68 and 70 are connected by passage 72 to lumens 74 and 76 which are in communication with lumen 78 of rectangular tube 38, which in turn is in communication via means within probe handle portion 12 with tube 28 and therethrough with vacuum source 106. Tube 38 and the proximal portion 36 of electrode piece 34 are covered with a dielectric coating. Distal portion 80 of electrode 34 is offset from proximal portion 36 angle 82.

Electrode 34 is formed of a monolithic, homogeneous metallic material such as stainless steel, titanium, nickel, or tungsten. Electrode 34 may be formed by machining from bar stock or from or a casting, however, a preferred method of manufacture is Metal Injection Molding (abbreviation "MIM"). Electrode 34 is molded complete with proximal portion 36 and distal portion 80 co-linear. This allows lumens 74 and 76 to be formed in the mold as cylindrical passages. After molding and sintering of electrode 34, electrode 34 is bent so that distal portion 80 is offset from proximal portion 36 at angle 82. This method of manufacture allows electrode 34 to be produced at low cost since no conventional machining is required.

Probe 10 is used in a more or less vertical orientation to remove a tissue portion from surrounding vascular tissue. Referring now to FIG. 12, during use, irrigant 83 supplied to the site via irrigation ports 58 and 60 flows down surface portions 42 and 50 respectively so as to bathe distal-most portion 84 and tissue in close proximity in conductive liquid. Liquid 85 is removed from the region via aspiration ports 68 and 70. When RF power is applied, tissue in contact with distal portion 44 of first surface portion 42 is vaporized, while tissue in contact with second surface portion 50 is desiccated so as to prevent bleeding. The relative portion of power used for vaporization and desiccation is determined by the amount of tissue in contact with the two regions of the electrode 34. This, in turn, is determined by the surgeon's technique, and more particularly, largely by the orientation of the probe relative to the motion with which the surgeon advances the probe into the tissue. For instance, in FIG. 12 depicting tissue portion 89 during removal from tissue bed 90, a separating force 92 is applied to portion 88. Probe 10 is used to separate portion 89 from bed 90. Probe 10 and electrode 34 are advanced into the tissue with a motion 93 which is at angle 88 to a perpendicular 94 to the axis of tube 38. This relative motion causes little tissue to be in contact with surface 50. This, in turn, causes most of the RF energy to be expended in vaporization of tissue at second surface 58. Desiccation of tissue at surface 50 is minimal.

Figure 14:
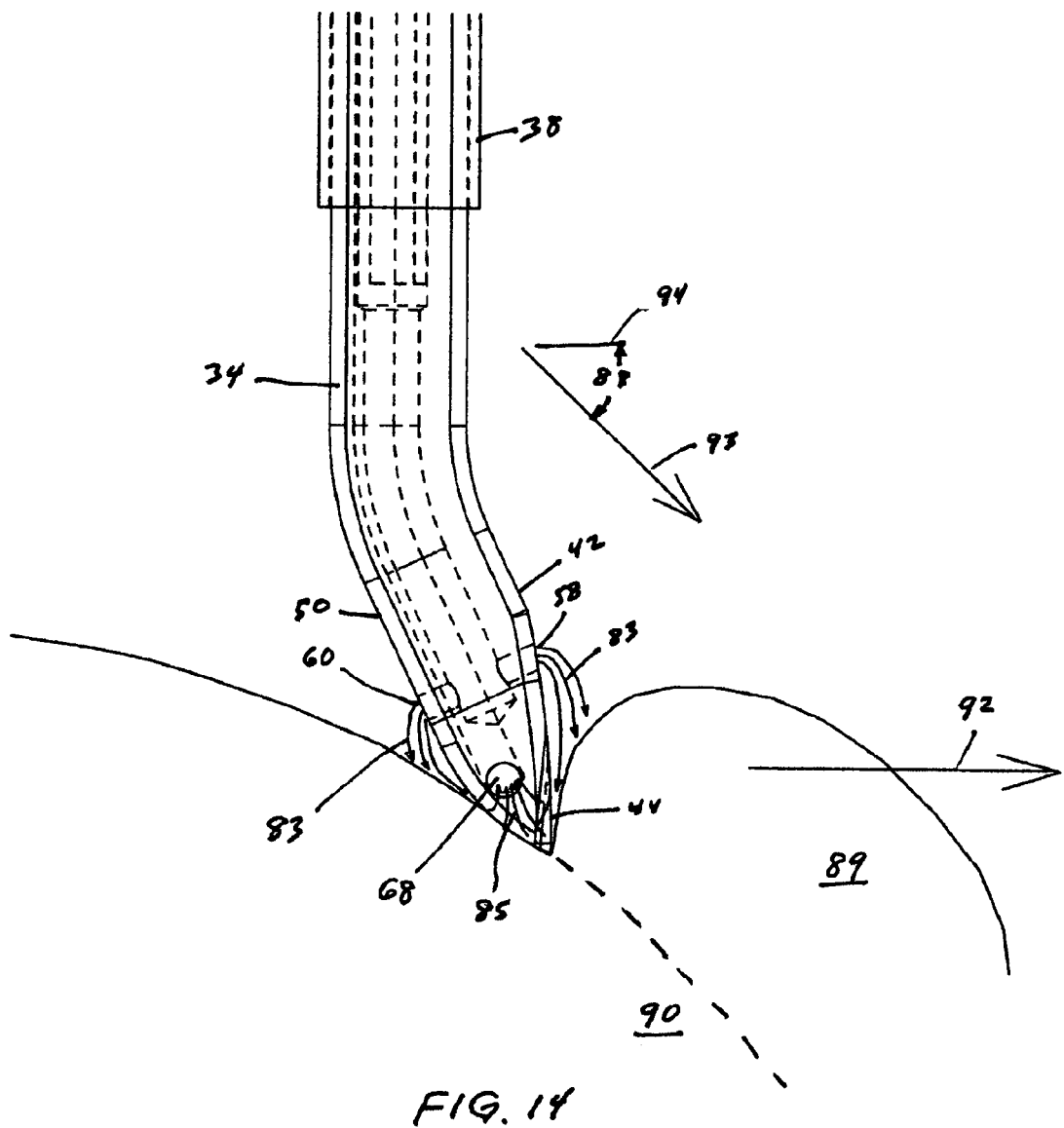
FIG. 14 is an expanded elevational view of the distal portion of the instrument of FIG. 2 during use when primarily cutting and coagulating tissue.

Referring now to FIG. 14 depicting the removal of tissue portion 89 from tissue bed 90, probe 10 is advanced into the tissue with motion 93 at angle 88 to perpendicular 94 to the axis of tube 38. This relative motion causes more tissue to be in contact with surface 50 thereby causing more desiccation of tissue in this region. This, in turn, causes decreased bleeding from the tissue bed which has been resected.

Figure 15:
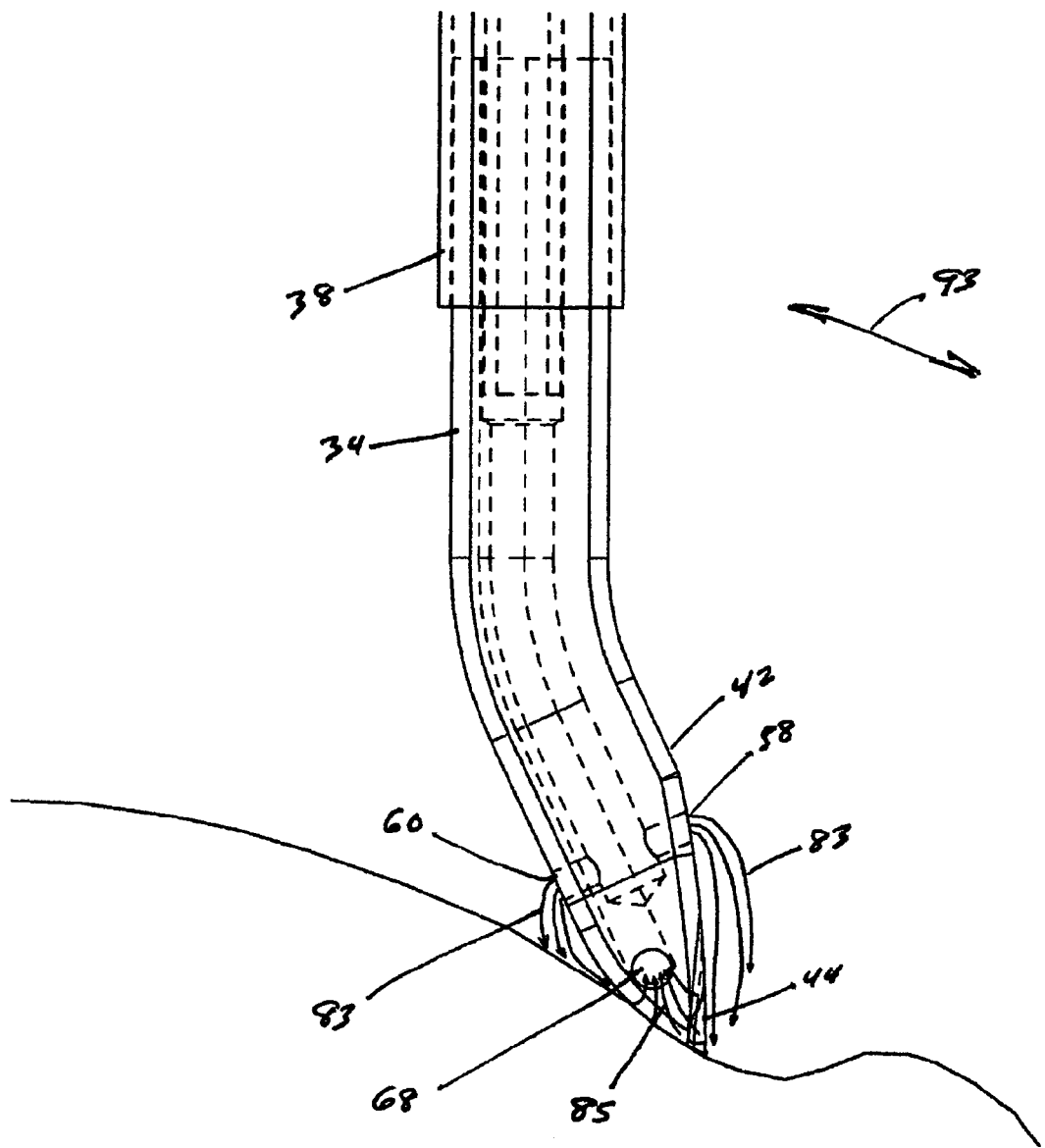
FIG. 15 is an expanded elevational view of the distal portion of the instrument of FIG. 2 during use when primarily coagulating tissue.

In FIG. 15 only surface 50 is in contact with tissue as the surgeon uses the probe tip to "paint" the surface to desiccate the tissue and stop bleeding. The relative motion imparted by the surgeon is essentially parallel to the resected surface. No tissue vaporization occurs.

In use, then, the surgeon is able to control the relationship between vaporization and desiccation through orientation of probe 10 and relative motion between the probe and tissue being resected. The probe can vaporize tissue aggressively with minimal desiccation, or can be used in a manner which produces more desiccation with less aggressive vaporization. The probe can also be used to desiccate resected surfaces by painting them with second surface 50.

Figure 16:
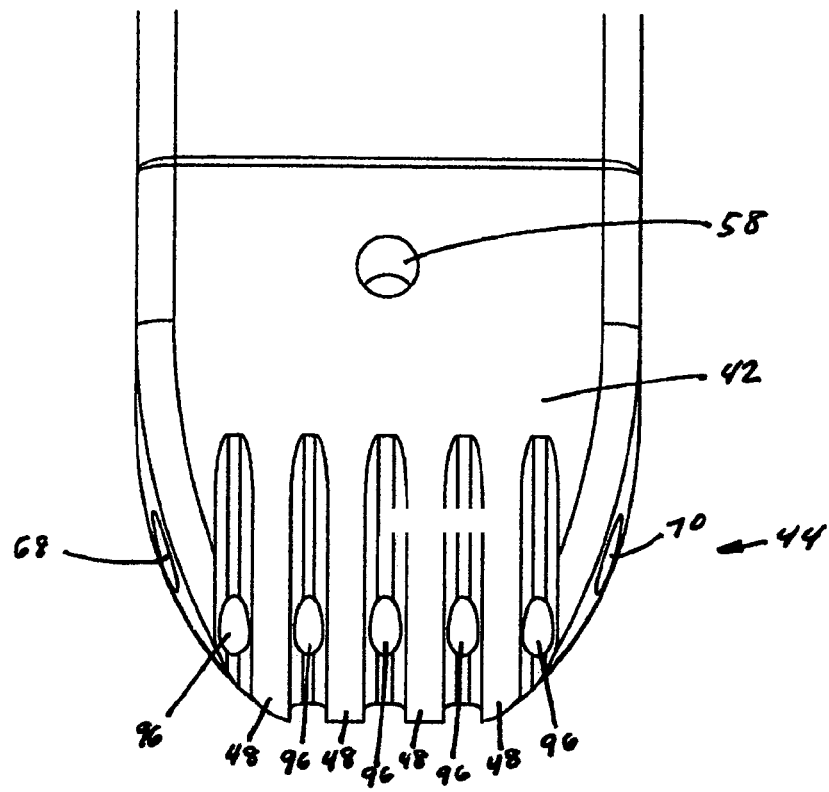
FIG. 16 is an expanded elevational view of the distal portion of an alternate embodiment.
Figure 17:
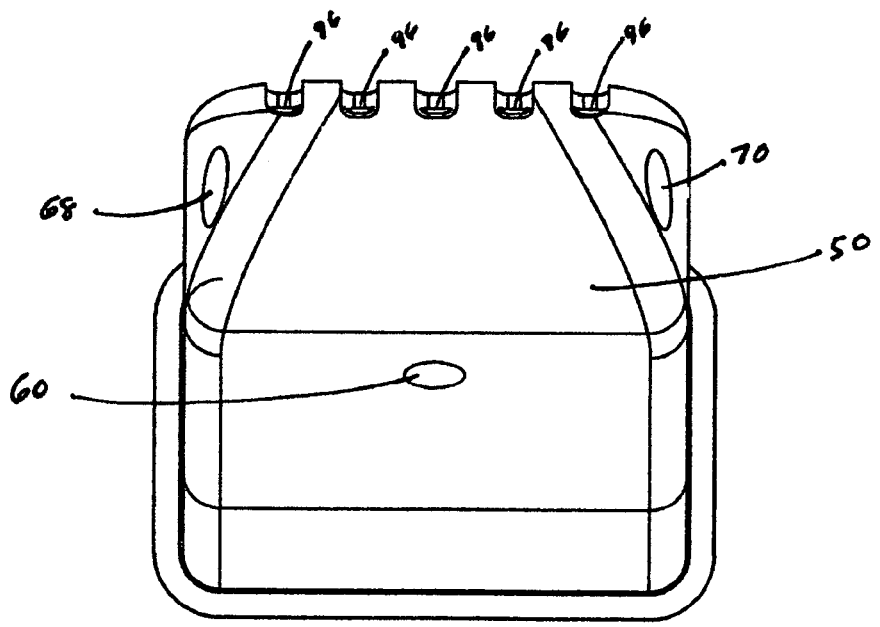
FIG. 17 is an distal axial view of the object of FIG. 16.

FIGS. 16 and 17 show the distal portion 44 of an alternate embodiment having additional aspiration ports 96 between ribs 48. Ports 96 are in communication with lumen 72 (FIG. 12) so as to provide additional aspiration of fluid. In other embodiments aspiration ports 68 and 70 are eliminated and all aspiration is through ports 96. In some applications aspiration is not required or is supplied by an external device. In other embodiments for such applications, probe 10 does not have an aspiration means.

Modifications may be made to the irrigation means of probe 10. For instance, in other embodiments irrigation is by a tubular member external to tube 38. In one embodiment the tubular member is coaxial with tube 38 and fluid is introduced through a gap between tube 38 and the external tube. In other embodiments a tube having an axis parallel to that of tube 38 is affixed to the external surface of tube 38 to create a flow path to distal end 22 of probe 10.

Distal portion 44 of first surface 42 has formed therein grooves 46 and ribs 48 configured to provide regions of high current density for enhanced vaporization of tissue. The ribs may have cross-sectional shapes other than the rectangular shape of the previously disclosed embodiments. For instance, the ribs may have triangular, trapezoidal or irregular cross-sections. Other protuberances having axes approximately normal to distal portion 44 of surface 42 may also be used to provide regions of high current density. These may include cylindrical protrusions, or protrusions having cross-sections which are triangular, trapezoidal, or irregular.

What is claimed:

1. A monopolar electrosurgical probe comprising
a handle having a proximal end and a distal end;
an insulated elongated member having a proximal end and a distal end, wherein the proximal end of said elongated member is affixed to the distal end of said handle;
a single conductive electrode having a proximal end and a distal end, wherein said proximal end is assembled directly to the distal end of said elongated member; said conductive electrode comprising first and second conductive surfaces that intersect to form a distal edge having an included angle ranging between 20 and 110 degrees, said first conductive surface having a distal portion in which are formed a plurality of protuberances that create regions of high current density for high efficiency vaporization of tissue and said second conductive surface having a smooth convex contour adapted for coagulating tissue.

2. The probe of claim 1 wherein said included angle ranges between 30 and 90 degrees.

3. The probe of claim 1, wherein said edge has a linear portion.

4. The probe of claim 1, wherein said edge is curvilinear.

5. The probe of claim 3, wherein said linear portion of said edge forms an angle with the axis of said elongated member between 30 and 90 degrees.

6. The probe of claim 5, wherein said linear portion of said edge forms an angle with the axis of said elongated member between 45 and 90 degrees.

7. The probe of claim 1, wherein said conductive electrode is formed of a monolithic homogeneous metallic material.

8. The probe of claim 1, further comprising an irrigation means for conducting fluid from an external source to the surgical site.

9. The probe of claim 8, wherein said irrigation means comprises at least one irrigation port in an exterior surface of said electrode.

10. The probe of claim 1, further comprising a means for aspirating fluid and debris from the surgical site.

11. The probe of claim 10, wherein said means comprises at least one aspiration port in an exterior surface of said electrode.

12. The probe of claim 1, wherein said protuberances comprise a series of parallel raised ribs separated by grooves.

13. The probe of claim 1, wherein said electrode is bent along its longitudinal axis such that the distal end of the electrode is offset from the proximal end of the electrode.

14. The probe of claim 1, wherein the included angle ranges between 20 and 30 degrees.

15. The probe of claim 1, wherein the proximal end of said single conductive electrode has a cross-section comprised of first and second opposing conductive surfaces separated by first and second lateral surfaces, said conducting and lateral surfaces tapering in the distal direction such that said first and second surfaces intersect to form said distal edge.

16. An electrosurgical system for the electrosurgical treatment of tissue in the presence of a conductive liquid comprising:
the electrosurgical probe of claim 1;
a power source; and
a means for applying high frequency voltage to said electrosurgical probe.

17. The system of claim 16, wherein said included angle ranges between 30 and 90 degrees.

18. The system of claim 16, wherein said edge has a linear portion.

19. The system of claim 16, wherein said edge is curvilinear.

20. The system of claim 18, wherein said linear portion of said edge forms an angle with the axis of said elongated member between 30 and 90 degrees.

21. The system of claim 20, wherein said linear portion of said edge forms an angle with the axis of said elongated member between 45 and 90 degrees.

22. The system of claim 16, wherein said conductive electrode is formed of a monolithic homogeneous metallic material.

23. The system of claim 16, further comprising an irrigation means for conducting fluid from an external source to the surgical site.

24. The system of claim 17, wherein said irrigation means comprises at least one irrigation port in an exterior surface of said electrode.

25. The system of claim 16, further comprising a means for aspirating fluid and debris from the surgical site.

26. The system of claim 16, wherein said protuberances comprise a series of parallel raised ribs separated by grooves.

27. A method of conducting an electrosurgical procedure comprising the steps of:
providing the electrosurgical probe of claim 1;
positioning said conductive electrode in the proximity of a tissue to be treated in the presence of an electrically conductive fluid;
applying a high frequency voltage to said conductive electrode to generate an electric field adjacent said first and second conductive surfaces; and
vaporizing the tissue to be treated with said first conductive surface and coagulating any remaining tissue with said second conductive surface.

28. The method of claim 27, wherein said included angle ranges between 30 and 90 degrees.

29. The method of claim 27, wherein said edge has a linear portion.

30. The method of claim 27, wherein said edge is curvilinear.

31. The method of claim 29, wherein said linear portion of said edge forms an angle with the axis of said elongated member between 30 and 90 degrees.

32. The method of claim 30, wherein said linear portion of said edge forms an angle with the axis of said elongated member between 45 and 90 degrees.

33. The method of claim 27, wherein said electrode is formed of a monolithic homogeneous metallic material.

34. The method of claim 27, further comprising an irrigation means for conducting fluid from an external source to the surgical site.

35. The method of claim 34, wherein said irrigation means comprises at least one irrigation port in an exterior surface of said electrode.

36. The method of claim 27, further comprising a means for aspirating fluid and debris from the surgical site.

37. The method of claim 36, wherein said means comprises at least one aspiration port in an exterior surface of said electrode.

38. The method of claim 27, wherein said protuberances comprise a series of parallel raised ribs separated by grooves.

* * * * *